United States Patent [19]
Schmitt

[11] Patent Number: 4,469,607
[45] Date of Patent: Sep. 4, 1984

[54] PYRROLIDINIUM METHANE SULFONATES AS SURFACTANTS IN ENHANCED OIL RECOVERY

[75] Inventor: Kirk D. Schmitt, Pennington, N.J.

[73] Assignee: Mobil Oil Corporation, New York, N.Y.

[21] Appl. No.: 373,551

[22] Filed: Apr. 30, 1982

[51] Int. Cl.$^3$ .............................................. E21B 43/22
[52] U.S. Cl. .......................... 252/8.55 D; 260/501.13; 166/274; 166/275
[58] Field of Search ............. 260/501.13; 252/8.55 D; 166/274, 275

[56] References Cited

U.S. PATENT DOCUMENTS

| | | | |
|---|---|---|---|
| 2,935,493 | 5/1960 | Schuller et al. | 260/501.13 |
| 3,839,425 | 10/1974 | Barlett | 260/501.13 |
| 3,939,911 | 2/1976 | Maddox et al. | 166/275 |
| 4,166,038 | 8/1979 | Stournas | 252/8.55 D |
| 4,193,452 | 3/1980 | Wilson et al. | 252/8.55 D |

OTHER PUBLICATIONS

Chem. Abstracts, vol. 96, No. 219688w, 1982.

*Primary Examiner*—Christine M. Nucker
*Attorney, Agent, or Firm*—Alexander J. McKillop; Charles J. Speciale; Michael G. Gilman

[57] ABSTRACT

There are provided pyrrolidinium methane sulfonates as surfactants in enhanced oil recovery.

6 Claims, No Drawings

PYRROLIDINIUM METHANE SULFONATES AS SURFACTANTS IN ENHANCED OIL RECOVERY

BACKGROUND OF THE INVENTION

This invention is directed to pyrrolidinium methane sulfonates as surfactants in enhanced oil recovery.

This invention relates to a method of increasing the recovery of oil from subterranean oil reservoirs and, more particularly, to waterflooding operations involving the injection of an aqueous solution or dispersion containing a surfactant solution.

In the recovery of oil from oil-bearing reservoirs, it usually is possible to recover only minor portions of the original oil in place by the so-called primary recovery methods which utilize only the natural forces present in the reservoir. Thus, a variety of supplemental recovery techniques has been employed in order to increase the recovery of oil from subterranean reservoirs. The most widely used supplemental recovery technique is waterflooding, which involves the injection of water into the reservoir. As the water moves through the reservoir, it acts to displace oil therein to a production system composed of one or more wells through which the oil is recovered.

It has long been recognized that factors such as the interfacial tension between the injected water and the reservoir oil, the relative mobilities of the reservoir oil and injected water, and the wettability characteristics of the rock surfaces within the reservoir are factors which influence the amount of oil recovered by waterflooding. Thus, it has been proposed to add surfactants to the flood water in order to lower the oil-water interfacial tension and/or to alter the wettability characteristics of the reservoir rock. Also, it has been proposed to add viscosifiers such as polymeric thickening agents to all or part of the injected water in order to increase the viscosity thereof, thus decreasing the mobility ratio between the injected water and oil and improving the sweep efficiency of the waterflood.

Processes which involve the injection of aqueous surfactant solutions are commonly referred to as surfactant waterflooding or as low tension waterflooding, the latter term having reference to the mechanism involving the reduction of the oil water interfacial tension. Thus far, many such waterflooding applications have employed anionic surfactants. For example, a paper by W. R. Foster entitled "A Low-Tension Waterflooding Process", Journal of Petroleum Technology, Vol. 25, Feb. 1973, pp. 205–210, describes a promising technique involving the injection of an aqueous solution of petroleum sulfonates within designated equivalent weight ranges and under controlled conditions of salinity. The petroleum sulfonate slug is followed by a thickened water slug which contains a viscosifier such as water-soluble biopolymer in a graded concentration in order to provide a maximum viscosity greater than the viscosity of the reservoir oil and a terminal viscosity near that of water. This thickened water slug is the followed by a driving fluid such as a field brine which is injected as necessary to carry the process to conclusion.

One problem encountered in waterflooding with certain of the anionic surfactants such as the sulfonates is the lack of stability of these surfactants in so-called "high brine" environment. These surfactants tend to precipitate from solution in the presence of monovalent salts such as sodium chloride in concentrations in excess of about 2 to 3 weight percent and in the presence of much lower concentrations of divalent metal ions such as calcium and magnesium ions. Typically, divalent metal ion concentrations of about 50 to 100 ppm and above cause precipitation of the petroleum sulfonates. The salinity of the surfactant slug is also significant with regard to interfacial tensions achieved through the use of petroleum sulfonates such as disclosed in the Foster paper. Even in the absence of divalent metal ions, optimum interfacial tensions are seldom achieved at salinities significantly in excess of 2 to 3 weight percent.

Various surfactant formulations which contain anionic sulfonates that tolerate high salinities and/or high divalent metal concentrations have been proposed for use in high brine environments. Thus, U.S. Pat. No. 3,827,497 and U.S. Pat. No. 3,890,239 disclose a surfactant composition comprising a mixture of an organic sulfonate and a sulfated or sulfonated oxyalkylated alcohol and a polyalkylene glycol alkyl ether. The sulfonate is exemplified by the formula

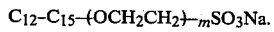

This is a sulfonate where m is an average of 3.

U.S. Pat. No. 4,216,097 teaches the use of sulfobetaines as agents in waterflooding.

SUMMARY OF THE INVENTION

There are provided pyrrolidinium methanesulfonates of the formula

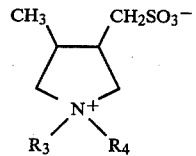

where $R_3$ and $R_4$ may be the same or different and may be alkyl (including alklaryl) or aryl, provided that $R_3$ and $R_4$ contain together at least ten (e.g., 10–20) carbon atoms.

There are also provided methods for using these pyrrolidinium methanesulfonates.

DETAILED DESCRIPTION

The pyrrolidinium methanesulfonates of the present invention are felt to be particularly useful as surfactants in enhanced oil recovery fluids. More particularly, these pyrrolidinium methanesulfonates are brine tolerant surfactants capable of producing low interfacial tensions between water and oil with or without an alcohol cosurfactant in the presence of salt concentrations, e.g., from 25% or less total salt and divalent ion concentrations from 200–20,000 ppm. Examples of alcohol cosurfactants include $C_5$–$C_7$ alcohols, especially hexanol.

The reaction of olefins with alkali metal bisulfite, in which the bisulfite adds across the double bond, is known. [M. S. Kharasch, E. M. May, F. R. Mayo, J. Org. Chem., 3, 175 (1938)]. The use of cosolvents [Norton et al, U.S. Pat. No. 3,522,297] and initiators [C. F. Norton, N. F. Seppi, and M. J. Reuter, J. Org. Chem., 33, 4158 (1968)] to promote this reaction is also known as is the use of a certain amount of final sulfonate product as solubilizer in those cases where the olefin is not water soluble [Chen et al U.S. Pat. No. 4,267,123].

It has been discovered, quite unexpectedly, that the course of the reaction is different when two double bonds are present in the same molecule in the relationship $X(CH_2CH=CHR)_2$. By way of illustration, it is known that allyl alcohol produces sodium 3-hydroxypropane sulfonate in high yield when treated with sodium bisulfite, air, and water. [R. F. Fischer, Ind. and Eng. Chem., 56, 41 (1964)]. This reaction is illustrated as follows.

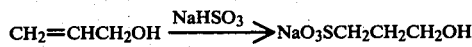

It would be expected that similar treatment of diallyl ether with two or more moles of bisulfite would lead to a disulfonate ether product as follows.

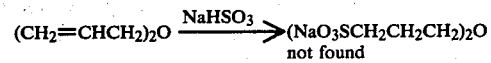

Instead, however, there is produced the unexpected tetrahydrofuran derivative as follows.

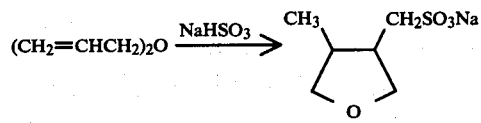

The compounds of this invention are readily prepared by reacting a bisulfite salt and air or oxygen with a diallyl compound, having the formula $X(CH_2CH=CHR)_2$, in an aqueous phase. The reaction proceeds generally at ambient conditions of temperature and pressure, although higher temperatures and pressures may be used if desired. The reaction is carried out in a homogenous aqueous phase. This phase can be water alone, if the olefinic reactant is water soluble. If not, this phase will be a mixture of water and sufficient cosolvent, such as $C_1$-$C_4$ alkanol to dissolve the olefinic reactant.

The bisulfite salt reactant may be any such reactable bisulfite salt such as sodium bisulfite, lithium bisulfite, potassium bisulfite, and ammonium bisulfite. This bisulfite salt may, thus, have the formula $MHSO_3$, where M is Na, Li, K or ammonium.

An oxygen containing gas acts as an initiator. It can be oxygen or air or other molecular oxygen containing gas.

The pyrrolidinium methanesulfonates of the present invention can be prepared by appropriate alkylation reactions, e.g.,

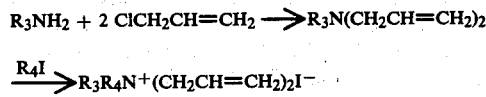

The following example illustrates the conditions which give rise to compounds of this invention.

EXAMPLE 1

A room temperature solution of 225 ml. $H_2O$, 225 ml. t-butyl alcohol and 43.2 g. diallyhexadecylmethylammonium iodide was stirred under a flow of 2 ml./min. air and a mixture of 34.2 g. $NaHSO_3$ and 9.8 g. $Na_2SO_3$ in 150 ml. $H_2O$ added over 2 hours. Nitrogen-14 NMR of the starting solution indicated a single peak at $-313$ ppm ($NO_3^- = 0$ PPM). Nitrogen-14 NMR of the reaction mixture at 2 hours indicated 90% conversion to another compound with a chemical shift of $-305$ ppm. After purification by chromatography on a Water's Associates Prep 500 liquid chromatograph there were obtained 20.6 g. white wax (53%) whose elemental analysis was consistent with the expected pyrrolidinium sulfonate of the following structure:

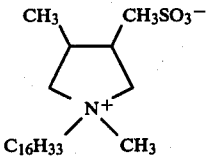

Calculated for $C_{23}H_{47}NSO_3$: C,66.13%; H,11.34%; N,3.35%; S,7.68%. Found: C,66.00%; H,10.53%; N,3.33%; S,7.34%.

Various types of amphoteric surfactants are known. One type is described in the Maddox et al U.S. Pat. No. 3,939,911 and is represented as follows:

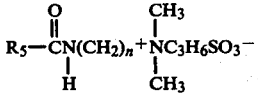

Another type of amphoteric surfactant is described in the Wilson et al U.S. Pat. No. 4,193,452 and is represented as follows:

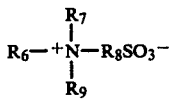

The above-illustrated surfactants of the Maddox et al patent are to be used in conjunction with at least two other surfactants, and the above-illustrated surfactants of the Wilson et al patent are to be used in conjunction with alcohol co-surfactant.

The surprising solubility properties of surfactants according to the present invention are revealed by comparing properties of a compound of the present invention according to the formula

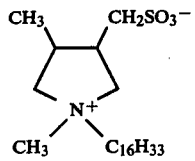

with properties of a compound according to the Wilson et al U.S. Pat. No. 4,193,452 according to the formula

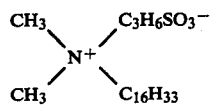

This comparison is described in the following examples:

EXAMPLE 2

Solubilities were measured by attempting to dissolve 2% weight/volume of sulfonate in a brine containing NaCl to CaCl₂ to MgCl₂ in weight ratio 13.2:2.6:0.8 over a total solids range of 0 to 28%. The compound of the present invention was soluble to 2% over this entire range while the compound of the Wilson et al patent was only soluble in a narrow range from 12 to 19% total dissolved solids. The compound of the present invention could be dissolved to 10% over the range 0-20% total dissolved solids while the compound of the Wilson et al patent could not be dissolved at such a high concentration at any brine concentration. The increased solubility due to the pyrrolidinium group is all the more unexpected when it is realized that the compound of the present invention contains a total of 23 carbon atoms compared to 21 for the compound of the Wilson et al patent. An increase in carbon atoms would ordinarily be expected to produce a decrease in water solubility.

To demonstrate the surfactant properties of surfactants of the present invention, surfactants were dissolved in brines whose NaCl:CaCl₂:MgCl₂ compositions were as described above and the interfacial tensions of the surfactant solution measured against crude oil by the spinning drop method described by Wade in *Adsorption at Interfaces*, ACS Symp. #8, pp. 234-247 (1975). These procedures are discussed in the following Examples 3-5.

EXAMPLE 3

A solution containing 12% brine, 2% surfactant of the formula

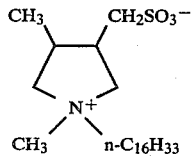

and 0.57% hexanol was equilibrated with oil and the interfacial tension measured against crude oil. The interfacial tension was 33 millidyne/cm.

EXAMPLE 4

Example 4 was the same as Example 3, but 16.6% brine was used and the interfacial tension was 6 millidyne/cm.

EXAMPLE 5

Example 5 was the same as Example 3, but the brine was 22% and the surfactant had the formula

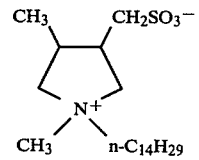

The interfacial tension was 13 millidyne/cm.

The present invention may be carried out utilizing injection and production systems as defined by any suitable arrangement of wells. One well arrangement commonly used in waterflooding operations and suitable for use in carrying out the present invention is an integrated five-spot pattern of the type illustrated in U.S. Pat. No. 3,927,716 to Burdyn et al. Other well arrangements may be used in carrying out the present invention, examples of which are set forth in the Burdyn et al patent. The patents and literature articles cited herein are hereby expressly incorporated herein by reference.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A method for the recovery of oil from a subterranean oil reservoir penetrated by spaced apart injection system and production system in which an aqueous surfactant fluid is injected into the reservoir via the injection system to displace oil to the production system, said method comrising injecting into said reservoir an aqueous fluid comprising dissolved surfactant in an amount sufficient to enhance the recovery of oil, said surfactant being a compound according to the formula

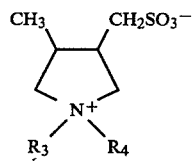

where R₃ and R₄ may be the same or different and may be alkyl or aryl, provided that R₃ and R₄ contain together at least ten carbon atoms.

2. A method according to claim 1, wherein R₃ and R₄ contain together less than 20 carbon atoms.

3. A method according to claim 1, wherein R₃ is CH₃ and R is n-C₁₆H₃₃.

4. A method according to claim 1, wherein R₃ is CH₃ and R₄ is n-C₁₄H₂₉.

5. A method according to claim 1, wherein said injected aqueous fluid further comprises brine, said brine having a salt concentration of from about 25% or less total salt and a divalent ion concentration of from about 200 to about 20,000 ppm.

6. A method according to claim 1, wherein said injected aqueous fluid further comprises an alcohol cosurfactant containing from 5 to 7 carbon atoms.

* * * * *